(12) United States Patent
Reyneke

(10) Patent No.: US 11,649,199 B2
(45) Date of Patent: May 16, 2023

(54) REFRIGERATION RECOVERY FROM REACTOR FEED IN A PROPANE DEHYDROGENATION SYSTEM

(71) Applicant: KELLOGG BROWN & ROOT LLC, Houston, TX (US)

(72) Inventor: Rian Reyneke, Katy, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 17/692,597

(22) Filed: Mar. 11, 2022

(65) Prior Publication Data

US 2022/0194876 A1    Jun. 23, 2022

Related U.S. Application Data

(62) Division of application No. 17/016,530, filed on Sep. 10, 2020, now Pat. No. 11,306,045.

(60) Provisional application No. 62/898,439, filed on Sep. 10, 2019.

(51) Int. Cl.
| | |
|---|---|
| *C07C 7/00* | (2006.01) |
| *C07C 7/09* | (2006.01) |
| *B01D 5/00* | (2006.01) |
| *B01D 3/14* | (2006.01) |
| *C07C 7/04* | (2006.01) |

(52) U.S. Cl.
CPC ............. *C07C 7/005* (2013.01); *B01D 3/143* (2013.01); *B01D 5/006* (2013.01); *C07C 7/04* (2013.01); *C07C 7/09* (2013.01)

(58) Field of Classification Search
None
See application file for complete search history.

(56) References Cited

U.S. PATENT DOCUMENTS

| | | |
|---|---|---|
| 2,938,934 A | 5/1960 | Williams |
| 2,953,905 A | 9/1960 | Chrones et al. |
| 3,309,882 A | 3/1967 | Cabanaw |
| 3,996,030 A | 12/1976 | Scheibel |
| 4,121,917 A | 10/1978 | Baker et al. |
| 4,897,098 A | 1/1990 | Pate et al. |
| 5,600,049 A | 2/1997 | Sy |
| 6,271,433 B1 | 8/2001 | Keady et al. |
| 6,291,734 B1 * | 9/2001 | Stork ................. C10G 7/00 585/809 |
| 9,909,804 B2 * | 3/2018 | Sumner ............... F25J 3/0219 |
| 2006/0004242 A1 * | 1/2006 | Verma ............... C10G 70/043 585/809 |
| 2006/0135840 A1 | 6/2006 | Reyneke et al. |

(Continued)

FOREIGN PATENT DOCUMENTS

WO    2018125359 A1    7/2018

OTHER PUBLICATIONS

International Search Report and Written Opinion dated Nov. 30, 2020 for International Application No. PCT/US20/50049 filed Sep. 10, 2020; 10 pages.

*Primary Examiner* — Tam M Nguyen
(74) *Attorney, Agent, or Firm* — Gary M. Machetta

(57) ABSTRACT

A method to recover refrigeration credit from propane feed to a propane dehydrogenation reactor by fully condensing a Depropanizer overhead stream, letting the condensed stream down in pressure, and vaporizing the stream at lower pressure against process streams to recover refrigeration credit.

4 Claims, 1 Drawing Sheet

(56) References Cited

U.S. PATENT DOCUMENTS

| | | |
|---|---|---|
| 2010/0025218 A1 | 2/2010 | Panditrao |
| 2014/0260419 A1* | 9/2014 | Steacy .................... C07C 5/327 62/617 |
| 2015/0052940 A1 | 2/2015 | King et al. |
| 2018/0185766 A1 | 7/2018 | King et al. |
| 2018/0265430 A1 | 9/2018 | Kim et al. |
| 2019/0048751 A1 | 2/2019 | Noureldin et al. |
| 2019/0049175 A1 | 2/2019 | Noureldin et al. |
| 2019/0204008 A1 | 7/2019 | Van Willigenburg |
| 2021/0070675 A1 | 3/2021 | Reyneke |
| 2021/0070676 A1* | 3/2021 | Reyneke .................. C07C 7/04 |

* cited by examiner

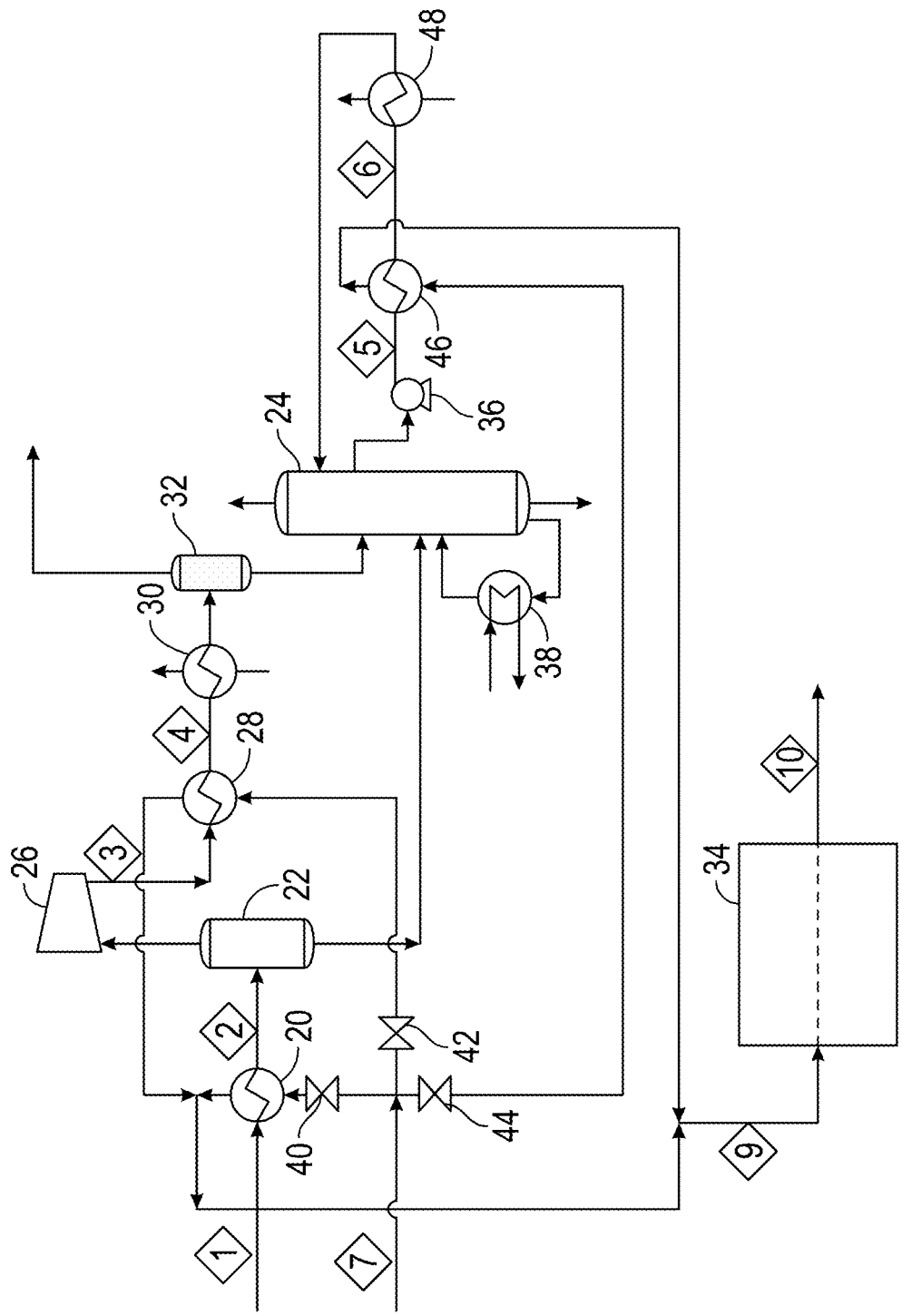

REFRIGERATION RECOVERY FROM REACTOR FEED IN A PROPANE DEHYDROGENATION SYSTEM

CROSS-REFERENCES TO RELATED APPLICATIONS

This application is a divisional application from U.S. patent application Ser. No. 17/016,530 filed Sep. 10, 2020, now U.S. Pat. No. 11,306,045, which claims the benefit of U.S. Provisional Patent Application Ser. No. 62/898,439 filed Sep. 10, 2019, both of which are incorporated herein in their entireties by reference.

TECHNICAL FIELD

The present invention relates to a process for recovering propylene from a propane dehydrogenation (PDH) process, and more particularly relates to recovering refrigeration from reactor feed in a PDH process.

BACKGROUND

Propane dehydrogenation (PDH) is a process step in the production of propylene from propane. PDH is important to the petrochemical industry because propylene is the second most important starting product in the petrochemical industry after ethylene. The purpose of a deethanizer and chilling train systems in a PDH process is to separate the cracked gas into a methane-rich tail gas product, a C2 process stream and a C3 process stream.

It would always be beneficial to improve a PDH process, such as by reducing refrigeration power requirements and/or reducing the size and cost of the compressor system. In particular, the refrigeration power required to provide process cooling in the −5 to 30° C. range typically is high. Presently, the depropanizer column overhead stream is produced as a vapor product, which feed to the reactor system without recovery of refrigeration. Process cooling in the −5 to 30° C. range is provided through propylene refrigeration.

BRIEF DESCRIPTION OF THE DRAWINGS

FIG. 1 is a non-limiting, schematic illustration of a portion of a PDH process as described herein.

SUMMARY

In one non-limiting embodiment, there is provided a process for recovering propylene from a propane dehydrogenation process, where the process includes partially or fully condensing a depropanizer overhead stream against a relatively warm cooling medium at relatively high pressure; letting down the liquid overhead stream in pressure; and partially or fully vaporizing the liquid overhead stream against at least one process stream to provide refrigeration.

In another non-restrictive version, there is provided a system for recovering propylene from a propane dehydrogenation process, where the system includes a depropanizer column generating a depropanizer overhead stream, at least one condenser for partially or fully condensing the depropanizer overhead stream, at least one device for letting down the pressure of the depropanizer overhead stream as determined by back-pressure of a reactor, and at least one chiller for partially or fully vaporizing the depropanizer overhead stream.

DETAILED DESCRIPTION

In a typical propane dehydrogenation process, fresh propane-rich feed as well as the propane-rich recycle from a C3 Splitter passes through a Depropanizer column to remove C4+ components. The purified propane-rich stream is recovered as a vapor overhead product that feeds directly to the reactor system without refrigeration heat recovery.

In one non-limiting embodiment, it has been discovered that the Depropanizer column overhead stream may be partially or fully condensed against a relatively warm cooling medium such as cooling water at relatively high pressure. In one non-limiting embodiment, "relatively warm" is defined as between about 20° C. independently to about 50° C., alternatively between about 28° C. independently to about 34° C.; where the term "independently" when used with reference to a range means any threshold may be used with any other threshold to give a suitable alternative range. In another non-restrictive version "relative high pressure" is defined as between about 10 independently to about 20 barg; alternatively between about 12 barg independently to about 15 barg. Other cooling media besides water may include, but not necessarily be limited to, air cooling.

The liquid overhead stream is then let down in pressure (based on back-pressure from the reactor) and vaporized against process streams to provide refrigeration in the temperature range of about −10° C. independently to about +30° C.; alternatively of about −5° C. independently to about 10° C., and offset the requirement for refrigeration typically provided by a propylene or propane refrigeration system in the same temperature range.

In more detail, and with reference to FIG. 1, dry process gas 1 from a Process Gas Dryer (not shown—coming from the left of FIG. 1) is chilled against Propane in First Deethanizer Feed Chiller 20 and sent to the First Deethanizer Feed Drum 22 as gas 2. Liquid from First Deethanizer Feed Drum 22 is fed to Deethanizer column 24. The overhead vapors go to Process Gas Compressor (PGC) 26. The discharge gas 3 from Process Gas Compressor 26 is cooled and partially condensed against propane in Second Deethanizer Feed Chiller 28, and is sent as stream 4 followed by chilling by propylene refrigerant in Third Deethanizer Feed Chiller 30 and sent to Second Deethanizer Feed Drum 32. Liquid from Second Deethanizer Feed Drum 32 is fed to Deethanizer 24 column. Also shown is Deethanizer Reboiler 38.

A pumparound on the Deethanizer Column 24 upper section 5 via pump 36 uses propane in Deethanizer First Side Cooler 46 and mid-level propylene refrigerant 6 in Deethanizer Second Side Cooler 48 to reduce the requirement for low-level refrigerant on an overhead condenser.

Liquid Propane 7 from the Depropanizer Column overhead stream (coming from the left of FIG. 1—Depropanizer not shown) is let down in pressure (as determined by reactor back-pressure), in one non-limiting embodiment by using valves 40, 42, and 44, and fully vaporized in the combination of Second Deethanizer Feed Chiller 28, First Deethanizer Feed Chiller 20 and Deethanizer First Side Cooler 46. Vaporized propane 9 from the chillers is routed to Cold Box 34 to be reheated and from the Cold Box 34 to the reactor as propane stream 10.

Non-limiting examples of stream information are given in Table I, whereas non-limiting examples of duties for the chillers are given in Table II.

TABLE I

EXAMPLE STREAM INFORMATION

| Stream Number | | 1 | 2 | 3 | 4 | 5 | 6 | 7 | 9 | 10 |
|---|---|---|---|---|---|---|---|---|---|---|
| Description | Units | Gas to 20 | Gas from 20 | Gas to 28 | Gas from 28 | From 36 to 46 | From 46 to 48 | Propane from Depropanizer | Propane from chillers | Propane from cold box 34 |
| Vapor Fraction | | 1.00 | 0.78 | 1.00 | 0.80 | 0.00 | 0.00 | 0.00 | 1.00 | 1.00 |
| Temperature | °C. | 10.0 | −1.8 | 29.7 | −1.6 | 14.2 | 4.3 | 42.3 | −5.7 | 38.0 |
| Pressure | $kg/cm^2$ | 13.9 | 13.7 | 21.9 | 21.7 | 12.8 | 12.8 | 15.0 | 4.0 | 3.9 |
| Mass Density | kg/cum | 15.8 | 20.1 | 18.1 | 24.0 | 497.6 | 513.2 | 462.6 | 8.6 | 6.8 |
| Total Mass Flow | kg/hr | 121969 | 121969 | 75698 | 75698 | 500000 | 500000 | 194605 | 194605 | 194605 |

TABLE II

EXAMPLE DUTIES

| Duties | Gcal/h |
|---|---|
| First Deethanizer Feed Chiller 20 | 4.7 |
| Second Deethanizer Feed Chiller 28 | 4.0 |
| Deethanizer First Pumparound Cooler 46 | 3.1 |
| Cold Box (propane) 34 | 3.6 |

Use of the propane feed to the reactor for refrigeration recovery as described herein substantially reduces the requirements for refrigeration from a propylene or propane refrigeration system, and could reduce the size and cost of the compressor system. In one non-limiting embodiment the refrigeration requirements may be reduced by about 50% or more, alternatively by about 30% or more. In a different non-restrictive version the reduction in the cost of the compressor system may be about 30%, alternatively about 20%.

In the foregoing specification, the invention has been described with reference to specific embodiments thereof. However, the specification is to be regarded in an illustrative rather than a restrictive sense. For example, equipment, processes, and operating conditions falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, there may be provided a process for recovering propylene from a PDH process, where the process consists essentially of or consists of: partially or fully condensing a depropanizer overhead stream against a relatively warm cooling medium at relatively high pressure; letting down the liquid overhead stream in pressure; and partially or fully vaporizing the liquid overhead stream against at least one process stream to provide refrigeration.

There may also be provided a system for recovering propylene from a propane dehydrogenation process, where the system consists essentially of or consists of a depropanizer column generating a depropanizer overhead stream; at least one condenser for partially or fully condensing the depropanizer overhead stream; at least one device for letting down the pressure of the depropanizer overhead stream as determined by back-pressure of a reactor; and at least one chiller for partially or fully vaporizing the depropanizer overhead stream.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

The invention claimed is:

1. A system for recovering propylene from a propane dehydrogenation process, the system comprising:
   a depropanizer column generating a depropanizer overhead stream;
   at least one condenser for partially or fully condensing the depropanizer overhead stream against a relatively warm cooling medium at a temperature between about 20° C. and about 50° C.;
   at least one device for letting down the pressure of the depropanizer overhead stream as determined by back-pressure of a reactor; and
   at least one chiller for partially or fully vaporizing the depropanizer overhead stream.

2. The system of claim 1, wherein the device is a valve.

3. The system of claim 1, wherein the chiller is configured such that refrigeration of the chiller is in the range of about −10 to about 30° C.

4. The system of claim 1, wherein the at least one condenser is configured to partially or fully condense the depropanizer overhead stream at a relatively high pressure is between about 10 and about 20 barg.

\* \* \* \* \*